(12) United States Patent
Jeng et al.

(10) Patent No.: US 8,106,254 B2
(45) Date of Patent: Jan. 31, 2012

(54) HEAT- AND ETHYLENE-INDUCIBLE FRUIT SPECIFIC PROMOTER

(75) Inventors: Shih-Tong Jeng, Taipei (TW); Yu-Hui Chen, Taipei (TW)

(73) Assignee: Council of Agriculture, Executive Yuan, Taipei (TW)

( * ) Notice: Subject to any disclaimer, the term of this patent is extended or adjusted under 35 U.S.C. 154(b) by 252 days.

(21) Appl. No.: 12/640,384

(22) Filed: Dec. 17, 2009

(65) Prior Publication Data

US 2010/0170014 A1    Jul. 1, 2010

(30) Foreign Application Priority Data

Dec. 30, 2008  (TW) .............................. 97151389 A

(51) Int. Cl.
| | | |
|---|---|---|
| *C12N 15/82* | (2006.01) | |
| *C12N 15/10* | (2006.01) | |
| *C12N 15/63* | (2006.01) | |
| *C07H 21/04* | (2006.01) | |
| *A01H 5/00* | (2006.01) | |

(52) U.S. Cl. ..... 800/287; 800/278; 800/295; 435/320.1; 435/468; 536/24.1; 536/23.1

(58) Field of Classification Search ..................... None
See application file for complete search history.

(56) References Cited

OTHER PUBLICATIONS

Piotr Chomczynski et al., Single-Step Method of RNA Isolation by Acid Guanidinium Thiocyanate-Phenol-Chloroform Extraction, Analytical Biochemistry, 1987, 156-159, vol. 162.

Yao-Guang Liu et al., Efficient isolation and mapping of Arabidopsis thaliana T-DNA insert junctions by thermal asymmetric interlaced PCR, 1995, 457-463, vol. 8.

Diego Orzaez et al., Agroinjection of Tomato Fruits. A Tool for Rapid Functional Analysis of Transgenes Directly in Fruit, Jan. 3-11, 2006, vol. 140.

*Primary Examiner* — Brent T Page
(74) *Attorney, Agent, or Firm* — WPAT, P.C.; Anthony King

(57) ABSTRACT

The present invention relates to a heat- and ethylene-inducible plant specific promoter, and its relevant recombinant plasmids and transgenic plants.

21 Claims, 3 Drawing Sheets
(1 of 3 Drawing Sheet(s) Filed in Color)

SEQUENCE LISTING

<160> NUMBER OF SEQ ID NOS: 9

<210> SEQ ID NO 1
<211> LENGTH: 2102
<212> TYPE: DNA
<213> ORGANISM: Lycopersicon esculentum
<220> FEATURE:
<221> NAME/KEY: promoter
<222> LOCATION: (1)..(2102)

<400> SEQUENCE: 1

| | | | | | |
|---|---|---|---|---|---|
| aacaagggt | gtttttttat | ttttcaacac | atctatcaag | gataagtttg | taaacatctt | 60 |
| aatattcaag | agttactcca | tccgttttat | aaagaatggt | ctagtttgac | ttggtatgga | 120 |
| gtttaagaaa | aataaagaag | acttttgatc | atgtggtcct | aaattaaagt | aatgttaaat | 180 |
| gtacaaaatt | gtcttttaat | cttgtggcct | taaacatgct | acgtggaaag | ttttaccaa | 240 |
| aagaaaagga | ggtcattctt | ttttaaata | gactaaaaag | aaaaggaggt | cattcttttt | 300 |
| gaaacggaag | gagtagtagc | tttcttaatg | ggtatgtcca | aaataaaaac | atcacttgtt | 360 |
| tggaaatgaa | agaagtattt | ataatttagt | tgttggatgt | gggtgtaact | actattgcta | 420 |
| ttaaataatg | aaaactagtt | tgtgtatttc | atagtcacaa | aatttggttt | gttacacaac | 480 |
| aactttctgg | tcagcatctt | gatatattat | ttagaagcat | gtattcaatg | atgtgatcat | 540 |
| gttcaagggt | gcaaggtacg | tattggattg | ggttaccatg | tttcggatca | atattggatc | 600 |
| ggattgccat | gttttaacat | aatctataag | atcgaattgc | cacgttccga | aagcctggct | 660 |
| gtttgtgtta | atatttcgtg | agagaaccaa | ttatgtgcta | tataatgtga | gttatttgtt | 720 |
| gttcgtgtac | ttgttgacaa | tattgtatat | gttgagatac | attgtggata | gaagtattgg | 780 |
| gttgtcatgt | ttttgttgta | cttaataaac | tcgtgctctt | agtagcttgt | acctgttaga | 840 |
| ctagatcctt | ggggttgtta | gttactttgt | aattcttaac | tagttcgttg | aaaaagagct | 900 |
| cgtttataaa | gatttttatc | tctataacat | ctgtagttcg | ttaatttttc | acatgtttaa | 960 |
| acttttggat | atgagggttc | tcctatttag | gtgttagagt | gctgcccgca | tggcccggta | 1020 |
| gtttggttcg | taacaacata | atatttttaa | tatattcttt | ttctatttaa | gtttgatact | 1080 |
| aaagcaatga | ttttaaaaaa | ataaattgat | aagttgtatt | tatttaatag | gacagtgact | 1140 |
| tgaaaaatta | aattttagag | gtcaattggg | aaacatgtaa | aaaattatat | tattttttat | 1200 |
| tgaattattt | tcatttacta | tcttaaatat | tttagtagtt | taaagaaatt | attttaataa | 1260 |
| ataatatgct | atgcctctta | taacatgtaa | aaagttaaat | taacattgaa | aacacataaa | 1320 |
| attacatata | cccacaaccc | gtcctgccca | cgttagtttt | caaaatctca | cttcaacccg | 1380 |
| atcctcatcc | cactcgctcc | gcacaacctt | aaacccgccc | ctgcccacat | agccttaaac | 1440 |
| caccccgtcc | agcatccgtc | ccaccccatt | gtcatcccta | caagaatccc | acagtaacca | 1500 |
| agagcaaagc | aaaaagttct | atttcagatt | cgtcaccatc | ccttcctcaa | caattcatcg | 1560 |
| atattatttt | ctgcaagatt | gaaggattct | tcaagatttg | cctttgagaa | gatgaagaaa | 1620 |
| tttgagattt | agaaaacggc | atatagtgga | tttgattgta | accttagaaa | aagattatat | 1680 |
| ttaattggga | gtgatgtagg | gtaatttagt | cattttaaat | tttattcata | aattggttat | 1740 |
| tcagaattaa | gaattaagtt | atttcacctt | caatccgtat | aaaataatat | ataaattgac | 1800 |
| ttataactta | tatatgtgtt | aattatgtga | cactgtaatt | tgctaaacaa | acgtagtaat | 1860 |
| ttgtgtgttg | aattttatac | atgacataaa | aatgctatca | aacatggtaa | agcttatata | 1920 |
| aaatttaaa | acggaataac | tcaacccctta | ttcggtaact | aaactgcccc | taagtgttaa | 1980 | tagtatagag ctgttctgtt tagttagttc ttttaattat ttccactctc ctataaatgt    2040 attttgtact gccatcttgt ttatgacata gagaaaaaag atggcagttt acagcaaaaa    2100 ag                                                                  2102

<210> SEQ ID NO 2
<211> LENGTH: 32
<212> TYPE: DNA
<213> ORGANISM: Artificial
<220> FEATURE:
<223> OTHER INFORMATION: Specific primer.
<220> FEATURE:
<221> NAME/KEY: misc_binding
<222> LOCATION: (1)..(32)

<400> SEQUENCE: 2
tgctcgaaaa actgtcgtgt tcctagtaac gt                                 32

<210> SEQ ID NO 3
<211> LENGTH: 30
<212> TYPE: DNA
<213> ORGANISM: Artificial
<220> FEATURE:
<223> OTHER INFORMATION: Specific primer.
<220> FEATURE:
<221> NAME/KEY: misc_binding
<222> LOCATION: (1)..(30)

<400> SEQUENCE: 3
gatgcatctc gaactttgtc cacaatctcc                                    30

<210> SEQ ID NO 4
<211> LENGTH: 30
<212> TYPE: DNA
<213> ORGANISM: Artificial
<220> FEATURE:
<223> OTHER INFORMATION: Specific primer.
<220> FEATURE:
<221> NAME/KEY: misc_binding
<222> LOCATION: (1)..(30)

<400> SEQUENCE: 4
accctgtatt ttggcggtag aatgaatact                                    30

<210> SEQ ID NO 5
<211> LENGTH: 15
<212> TYPE: DNA
<213> ORGANISM: Artificial
<220> FEATURE:
<223> OTHER INFORMATION: Arbitrary degenerate primer.
<220> FEATURE:
<221> NAME/KEY: misc_binding
<222> LOCATION: (1)..(15)
<220> FEATURE:
<221> NAME/KEY: misc_feature
<222> LOCATION: (1)..(1)
<223> OTHER INFORMATION: n is a, c, g, or t

<400> SEQUENCE: 5
ntcgastwts gwgtt                                                    15

<210> SEQ ID NO 6
<211> LENGTH: 16
<212> TYPE: DNA
<213> ORGANISM: Artificial
<220> FEATURE:
<223> OTHER INFORMATION: Arbitrary degenerate primer.
<220> FEATURE:
<221> NAME/KEY: misc_binding

```
<222> LOCATION: (1)..(16)
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 6
ngtcgaswga nawgaa                                                 16

<210> SEQ ID NO 7
<211> LENGTH: 16
<212> TYPE: DNA
<213> ORGANISM: Artificial
<220> FEATURE:
<223> OTHER INFORMATION: Arbitrary degenerate primer.
<220> FEATURE:
<221> NAME/KEY: misc_binding
<222> LOCATION: (1)..(16)
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 7
wgtgnagwan canaga                                                 16

<210> SEQ ID NO 8
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_binding
<222> LOCATION: (1)..(32)

<400> SEQUENCE: 8
cttttttgct gtaaactgcc atctttttc tc                                32

<210> SEQ ID NO 9
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_binding
<222> LOCATION: (1)..(32)

<400> SEQUENCE: 9
aagggttgag ttattccgtt ttaaaatttt at                               32
```

HEAT- AND ETHYLENE-INDUCIBLE FRUIT SPECIFIC PROMOTER

FIELD OF THE INVENTION

The present invention relates to a heat- and ethylene-inducible plant specific promoter.

BACKGROUND OF THE INVENTION

Plant gene transfer technology continues to progress in recent years, and has become a new way to improve varieties of crops. Scientists can put a particular gene, named foreign gene, into a plant so that the plant expresses traits which would not be expressed originally. The process which transfers foreign genes into organisms is known as gene transfer. In the past, scientists must go through a lengthy breeding process to transfer the special gene into cultivated species, and the parents with the special gene also must be able to hybrid with the cultivated species. On the contrary, gene transfer technology does not have these restrictions. Once transgenic technology is established successfully, new varieties of crops, which can not be bred well by traditional breeding, will be bred efficiently with improved ability to reduce losses or increase production per unit area. In a variety of plant gene transfer methods, the more commonly used are gene gun method, agrobacterium-mediated gene transfer method and electroporation method. Gene transfer methods applicable to different plant species and tissues are not the same. At present, transgenic tomato is produced by agrobacterium-mediated gene transfer method. The first genetically modified crop allowed in the market was launched in the United States in 1994, which was the genetically modified tomato with extended period of consumption. Because the gene transfer efficiency and the renewable capacity of tomatoes are better than that of most economic crops, tomatoes have been considered as a model of transgenic crops, and are widely used in various types of basic science research and application issues.

Gene expression is an important step in regulating cell physiology. The promoter used mostly for the gene expression in plant transformation is tobacco mosaic virus 35S promoter that is expressed generally in various tissues and developmental stages of a plant. Hence, tobacco mosaic virus 35S promoter is not suitable for the tissue specific gene expression. It is also not suitable while the general gene expression may cause damage to the plant. Applying a promoter with tissue specificity and developmental stage specificity may be a good solution for the above conditions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1:
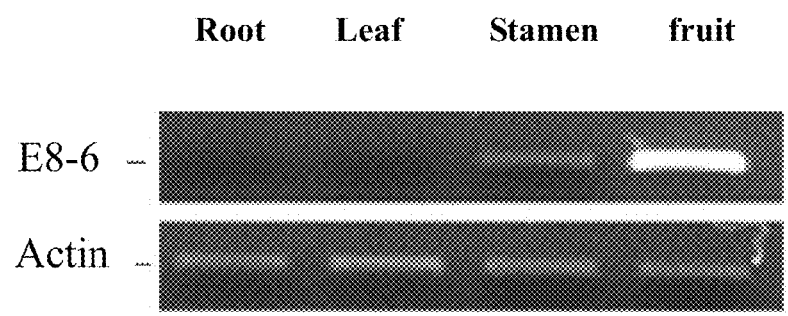
FIG. 1 shows expression of E8-6 gene in different parts of the tomato plants detected by RT-PCR method. The first row shows expression of E8-6 gene in tomato roots, leaves, stamens and fruits. The result shows that E8-6 gene is specifically expressed in stamens and fruits, particularly in fruits where a high volume of E8-6 gene expression is found. The second row shows expression of ACTIN gene as a control group, which indicates that the amount of RNA used for each analysis is about the same.
Figure 2:
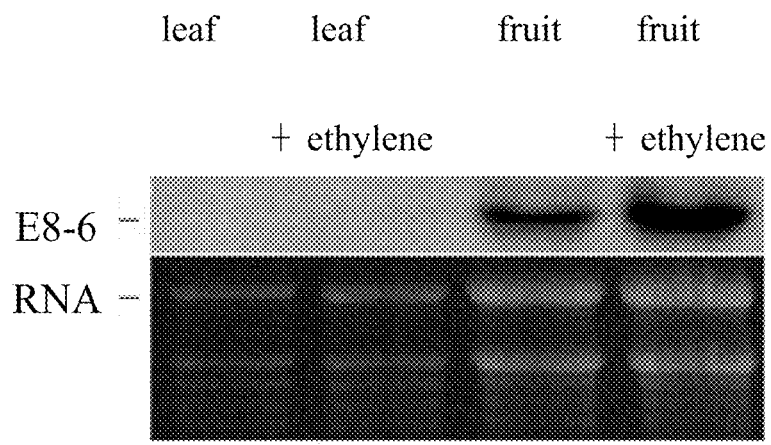
FIG. 2 shows the expression of E8-6 in different parts of the tomato plants detected by Northern blotting. The first row shows the expression of E8-6 gene in leaves and fruits with or without ethylene treatment. The result shows that E8-6 gene is only expressed in fruits, particularly in fruits with ethylene treatment where a high amount of E8-6 gene expression is found. Thus it is proved that E8-6 gene expression can be induced by ethylene. The second row shows expression of ribosomal RNA as a control group of sample analysis, which indicates the RNA relative volume used in analysis.
Figure 3:
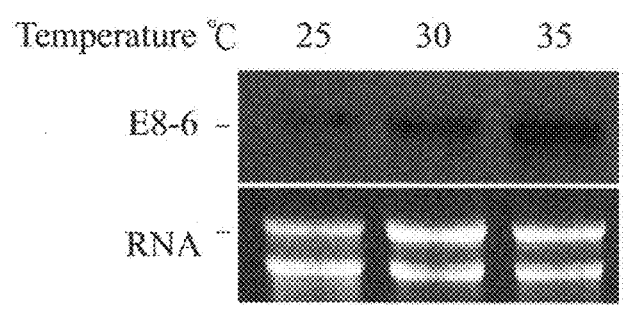
FIG. 3 shows the expression of E8-6 in tomato tissues detected by Northern blotting. The first row shows expression of E8-6 gene in tomatoes grown in 25, 30, or 35° C. The result shows that the expression of E8-6 gene is induced by temperature. The second row shows expression of ribosomal RNA as a control group of sample analysis, which indicates the RNA relative quantity used in analysis.
Figure 4:
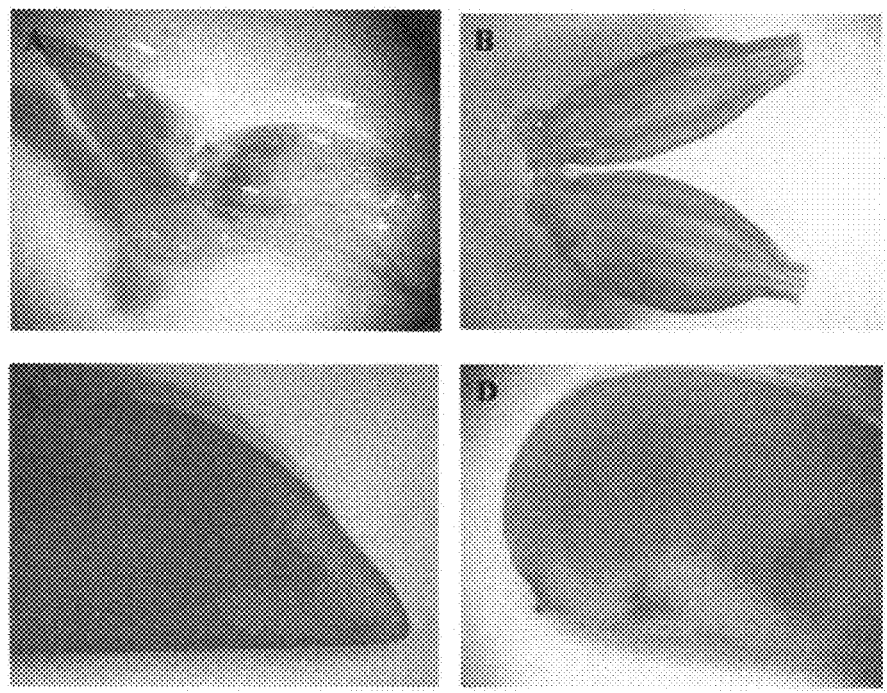
FIG. 4 shows E8-6 promoter activity analyzed by GUS staining in a tomato infected by agrobacterium. Plant tissue infection was mediated by agrobacterium LBA4404 with modified plasmid containing or not containing isolated E8-6 promoter fused with beta-glucunonidase (GUS) gene. (A) Four days after tomato flowers infected by agrobacterium with modified plasmid containing isolated E8-6 promoter fused with GUS, the expression of promoter in stamens is confirmed by GUS staining (cyan part in the figure). (B) Four days after tomato flowers infected by agrobacterium with modified plasmid not containing isolated E8-6 promoter fused with GUS. There is no background value in stamens determined by GUS staining (C) Four days after tomato fruits infected by agrobacterium with modified plasmid containing isolated E8-6 promoter fused with GUS, the expression of promoter in stamens is confirmed by GUS staining (cyan part in the figure). (D) Four days after tomato fruits infected by agrobacterium with modified plasmid not containing isolated E8-6 promoter fused with GUS. There is no background value in fruits determined by GUS staining.

The present invention relates to a heat- and ethylene-inducible plant specific promoter, and its relevant recombinant plasmids and transgenic plant.

DETAILED DESCRIPTION OF THE INVENTION

A series of plant genes are turned on by temperature. In the present invention, Suppression Subtractive Hybridization is used for isolation of cDNA E8-6, which is expressed considerably in tomatoes under high temperature (35° C.). The promoter of gene E8-6 is further isolated from the genome of tomatoes. The E8-6 promoter has the ability to stimulate the expression of down-stream genes under high temperature or ethylene treatment. Thus, the promoter can start the gene expression and produce a large amount of high-value protein specifically in plant fruits. The promoter can also be applied to enhancing the quality of fruits and increasing value added of crops.

The main technology of the present invention is to isolate the promoter of gene E8-6 and prove its activity by establishment of subtraction library, analysis of real-time polymerase chain reaction (real-time PCR), and isolation method of thermal asymmetric interlaced polymerase chain reaction (TAIL PCR), wherein the promoter consists of 2102 nucleotides and the nucleotide sequence is shown in SEQ ID NO: 1.

The present invention also proves that the promoter sequence of gene E8-6 isolated from tomatoes can considerably express genes under its control by transgenic plants and agrobacterium-mediated gene transfer method. It is also proved that gene expression is improved under high temperature or ethylene treatment The promoter of the present invention can considerably express genes under its control in fruits and stamens, and improve gene expression under high temperature or ethylene treatment, which has great application value in plant biotechnology. The promoter can produce a large amount of high-value protein in fruits, and the production of high-value protein in fruits can be improved by raising temperature or spraying ethylene. The promoter can also be applied to enhancing quality of fruits by expressing foreign proteins.

Therefore, the present invention provides a purified and isolated promoter which comprises a nucleotide sequence of SEQ ID NO: 1. Said promoter can specifically express a heterologous coding sequence operably linked to it in plants. In another embodiment, said promoter can be induced by temperature and ethylene to improve expression amount of the heterologous coding sequence operably linked to it.

In a preferred embodiment, the promoter specifically expresses a heterologous coding sequence operably linked to it in a specific plant region such as fruit or stamen. In a preferred embodiment, said heterologous coding sequence is for expressing foreign gene products. In a more preferred embodiment, the foreign gene is originated from bacteria, fungi, virus, animals, plants or fishes.

Said plant of the present invention comprises but not limited to flowering plants. In a preferred embodiment, the plant is *Lycopersicum esculentum*.

The present invention also provides a recombinant DNA vector which comprises a promoter as claimed in claim 1 and a heterologous coding sequence operably linked to the promoter. The heterologous coding sequence is for expressing foreign gene products. Said recombinant DNA vector can specifically express foreign gene products in a plant. In a more preferred embodiment, the foreign gene is originated from bacteria, fungi, virus, animals, plants or fishes. In a preferred embodiment, the recombinant DNA vector specifically express foreign gene products in specific plant region such as fruit or stamen.

The present invention further provides a transgenic plant comprising the promoter or the recombinant DNA vector described above. Said transgenic plant comprises but not limited to flowering plants. In a preferred embodiment, the transgenic plant is *Lycopersicum esculentum*.

EXAMPLES

The examples below are non-limiting and are merely representative of various aspects and features of the present invention.

Example 1

Establishment of Subtraction Library

Tomato species used in the examples were heat-tolerant tomato 5915 and heat-sensitive tomato 4783, which were both bred from tomato seeds provided by the Asian Vegetable Research and Development Center. The tomatoes have already been bred in the artificial climate chamber of the National Taiwan University, with day temperature 30° C. Collected the stamens individually and extracted their total RNA by the guanidine-hydrochloride method (Chomczynski P, Sacchi N., Single-step method of RNA isolation by acid guanidinium thiocyanate-phenol-chloroform extraction. *Anal. Biochem.* 1987 April; 162(1):156-9). Established the subtraction library by the clontech PCR-select cDNA subtraction kit (Clontech). Deduced the stamens mRNA of the heat-sensitive tomato 4783 at 30° C. from the stamens mRNA of heat-tolerant tomato 5915 to get the genes which can be expressed specifically by heat-tolerant tomatoes but not by the heat-sensitive ones.

Example 2

Real-Time PCR Analysis

The cDNA fragments that might participate in the interference at high temperature were recalled from the subtraction library and sequenced first. To know the preliminary functions of the genes, those sequences were compared with the database of web sites. Because there were a lot of cDNA fragments that might participate in the interference at high temperature from the subtraction library, the real-time PCR analysis was used to do fast selection to re-affirm the correlation between those potential cDNA fragments and high temperature.

Example 3

E8-6 Gene Expression in Tomatoes were Induced by Ethylene

Six similar size leaves and flowers in the florescence period of 5915 tomato plants were divided into two groups (each with three flowers and leaves respectively), then were put into two separated microcentrifuge tubes with ddH$_2$O. The tubes were then placed in a square breeding box. The wet paper towels were laid on the inner side of the breeding box's walls, and the ethephon (experimental group) or ddH$_2$O (control group) was sprayed on the towels. The breeding box was sealed with plastic wrap. The samples were took out after 6-hour light, frozen with liquid nitrogen and extracted RNA of the samples of experimental group and control group. Northern blotting was performed to analysis the E8-6 gene expression induced by ethylene in the leave films and flowers.

Example 4

The Promoter of Gene E8-6 was Isolated by Thermal Asymmetric Interlaced Polymerase Chain Reaction (TAIL PCR)

According to the proposed method of Liu et al. (Liu, Y. G., Mitsukawa, N., Oosumi, T., Whittier, R. F.(1995) Efficient isolation and mapping of *Arabidopsis thaliana* T-DNA insert junctions by thermal asymmetric interlaced PCR. Plant journal 8, 457-463), three reverse (3' to 5') specific primers (SP) were designed based on the known sequences: SP1 (TGCTC-GAAAAACTGTCGTGTTCCTAGTAACGT, SEQ ID NO:2), SP2 (GATGCATCTCGAACTTTGTCCA-CAATCTCC, SEQ ID NO:3), and SP3 (ACCCTG-TATTTTGGCGGTAGAATGAATACT, SEQ ID NO: 4).

Three arbitrary degenerate (AD) primers were also designed: AD1 (NTCGASTWTSGWGTT, SEQ ID NO:5), AD2 (NGTCGASWGANAWGAA, SEQ ID NO:6), and AD3 (WGTGNAGWANCANAGA, SEQ ID NO: 7). 1 uL genomic DNA, 0.6 uL each of said three AD primers, and 0.6 uL designed primer SP1, which is closest to the 3' end of the gene, were mixed with 13.7 uL ddH$_2$O, 2 uL 2.5 mM dNTP, 2 uL 10×PCR buffer, and 0.1 µL TaKaRa Taq, totally 20 uL for primary PCR. The resulting PCR product was 10-fold diluted for use. 1 uL PCR product from primary PCR, middle primer SP2, and three AD primers were used for secondary PCR. The resulting PCR product was 10-fold diluted for use. 1 uL PCR product from secondary PCR, primer SP3, which is closest to the 5' end of the gene, and three AD primers were used for tertiary PCR. Analysis of the final PCR product by Agarose gel electrophoresis resulted in one distinct and specific band. The band was cut and purified by Gel/PCR DNA Fragment Extraction Kit (Geneaid Biotech Ltd). After transformation, plating, culturing and DNA sequencing (MISSION BIOTECH, Taiwan), the nucleotide sequence of the promoter of gene E8-6 with 2102 bp sequence length was obtained, as shown in SEQ ID NO:1.

Example 5

The Plasmid Construction of E8-6 Promoter Promoting Expression of GUS Reporter Gene Primers CTTTTTTGCTGTAAACTGC-CATCTTTTTTCTC (SEQ ID NO: 8) and AAGGGT-TGAGTTATTCCGTTTTAAAATTTTAT (SEQ ID NO: 9) were designed from the nucleotide sequence of E8-6 promoter (SEQ ID NO: 1) obtained by TAIL PCR. With EcoR I and Nco I restriction site at both ends, respectively, the E8-6 promoter was cut from the genome of heat-tolerant tomato strain 5915 and amplified by PCR. The CaMV 35S promoter in front of the GUS reporter gene in the pCAMBIA 1301 vector was cut with restriction enzymes and replaced with the E8-6 promoter by DNA fragment annealing. The re-constructed vector was transformed into agrobacterium LBA4404 by electroporation.

Example 6

Gene Transfer Method with Agrobacterium Injection (Agroinjection)

According to the publication of Orzaez et al. (Orzaez, D., Mirabel, S.,; Wieland, W. H., Granell, A. (2006) Agroinjection of Tomato Fruits. A Tool for Rapid Functional Analysis of Transgenes Directly in Fruit. Plant physiology 140, 3-11), tomatoes were used as materials for performing a temporal gene transfer. The transformed agrobacterium LBA4404 were injected to the tomatoes with 1 ml syringe by inserting the syringe needle into the stigma of tomato fruit and into the calyx base of flower. The agrobacterium-injected plants were incubated at day/night temperature of 25/20° C. for 4 days, and then a GUS stain analysis was performed.

Example 7

The Promoter of Gene E8-6 Expressed GUS in *Arabidopsis thaliana* (with Ethylene or Heat-Shock Treatment)

Figure 5:
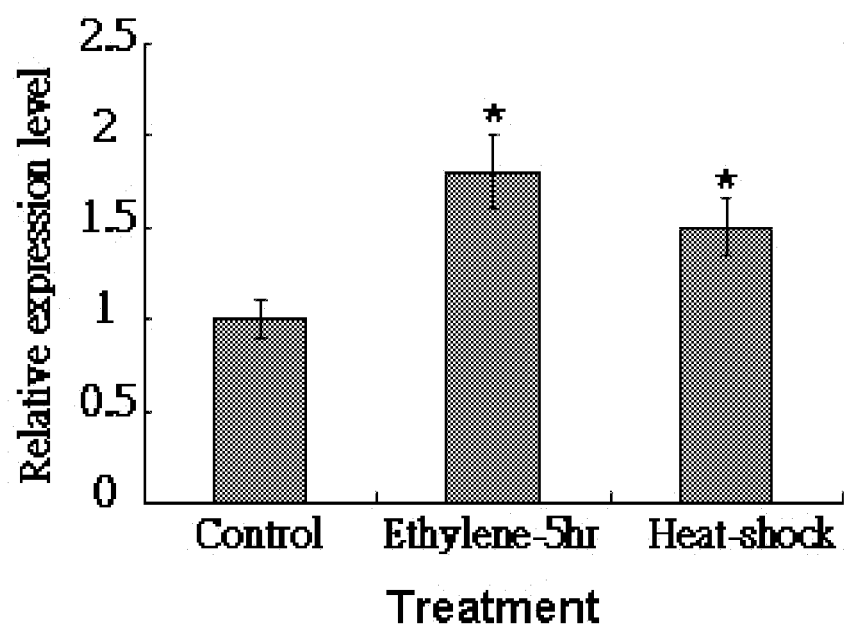
FIG. 5 shows comparison of GUS activity between T2 transgenic *Arabidopsis thaliana* (two-week-old), possessing the reporter gene GUS regulated by the promoter E8-6, with or without ethylene or heat-shock treatment. The figure shows that E8-6 promoter can be induced by ethylene or heat-shock and improve the expression of GUS. Statistic differences between control and ethylene or heat-shock treated plants are marked with stars when $p<0.05$ according to Student's test.

Three pots of T2 transgenic *Arabidopsis thaliana* (Col-0) (two-week-old) with GUS reporter gene regulated by E8-6 promoter were put into a square breeding box respectively. One pot was sprayed with ethephon, an ethylene releasing agent, as an ethylene treatment experimental group named "Ethylene-5 hr"; another pot was sprayed with ddH$_2$O as a control group and placed under light for 5 hours; the left pot was sprayed with ddH$_2$O and incubated in a growth chamber at 37° C. for 2 hours, then placed in a incubator (with a set environment for a photoperiod of 16 hours light and 8 hours dark, day temperature 25° C., night temperature 20° C.) overnight as a heat-shock treatment experimental group named "Heat-shock". After treatment, the overground parts of plants were clipped, from which the proteins were extracted to perform GUS activity assay. Relative fluorescence values were obtained, as shown in FIG. 5. In comparison with the control group, E8-6 promoter was induced by ethylene or temperature to improve the expression amount of GUS.

One skilled in the art readily appreciates that the present invention is well adapted to carry out the objects and obtain the ends and advantages mentioned, as well as those inherent therein. The cell lines, plants, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A purified and isolated promoter, comprising a nucleotide sequence of SEQ ID NO: 1.

2. The promoter of claim 1, which specifically expresses a heterologous coding sequence operably linked to the promoter in a plant.

3. The promoter of claim 2, which specifically expresses a heterologous coding sequence operably linked to the promoter in fruit or stamen of a plant.

4. The promoter of claim 3, wherein the plant is a flowering plant.

5. The promoter of claim 4, wherein the plant is *Lycopersicum esculentum*.

6. The promoter of claim 2, wherein the heterologous coding sequence is for expressing foreign gene products.

7. The promoter of claim 6, wherein the foreign gene is originated from bacteria, fungi, virus, animals, plants or fishes.

8. The promoter of claim 2, which is induced by temperature and ethylene to improve expression amount of the heterologous coding sequence operably linked to the promoter.

9. A recombinant DNA vector, comprising a promoter as claimed in claim 1 and a heterologous coding sequence operably linked to the promoter, wherein the heterologous coding sequence is for expressing foreign gene products.

10. The vector of claim 9, wherein the foreign gene is originated from bacteria, fungi, virus, animals, plants or fishes.

11. The vector of claim 9, which specifically expresses foreign gene products in a plant.

12. The vector of claim 11, which specifically expresses foreign gene products in fruit or stamen of a plant.

13. The vector of claim 12, wherein the plant is a flowering plant.

14. The vector of claim 13, wherein the plant is *Lycopersicum esculentum*.

15. The vector of claim 9, which is induced by temperature and ethylene to improve expression amount of the foreign gene products.

16. A transgenic plant, comprising the promoter as claimed in claim 1.

17. The transgenic plant of claim 16, which is a flowering plant.

18. The transgenic plant of claim 17, which is *Lycopersicum esculentum*.

19. A transgenic plant, comprising the recombinant DNA vector as claimed in claim 9.

20. The transgenic plant of claim 19, which is a flowering plant.

21. The transgenic plant of claim 20, which is *Lycopersicum esculentum*.

* * * * *